United States Patent
Hirono et al.

(10) Patent No.: US 6,635,896 B1
(45) Date of Patent: Oct. 21, 2003

(54) OPTICAL DISK STAMPER EXAMINATION MACHINE, OPTICAL DISK STAMPER EXAMINATION METHOD, AND OPTICAL DISK STAMPER

(75) Inventors: Kimio Hirono, Nirasaki (JP); Hirofumi Kurosawa, Chino (JP); Noboru Furuya, Chino (JP)

(73) Assignee: Seiko Epson Corporation, Tokyo (JP)

(*) Notice: Subject to any disclaimer, the term of this patent is extended or adjusted under 35 U.S.C. 154(b) by 0 days.

(21) Appl. No.: 09/173,181

(22) Filed: Oct. 15, 1998

(30) Foreign Application Priority Data

Oct. 28, 1997 (JP) .............................. 9-295488
Aug. 7, 1998 (JP) ........................... 10-224903

(51) Int. Cl.$^7$ .............................................. G01N 21/88
(52) U.S. Cl. .................... 250/559.4; 369/286
(58) Field of Search .................. 250/559.4, 559.44, 250/559.02, 221, 222.1, 201.5; 369/275.1, 275.5, 283, 286; 428/64.4

(56) References Cited

U.S. PATENT DOCUMENTS 4,327,830 A * 5/1982 Patel et al. .................. 206/303
5,126,180 A * 6/1992 Gotoh et al. ................ 369/288

FOREIGN PATENT DOCUMENTS

JP  5-151624  6/1993

* cited by examiner

Primary Examiner—John R. Lee
Assistant Examiner—Kevin Pyo
(74) Attorney, Agent, or Firm—Oliff & Berridge, PLC (57) ABSTRACT

A glass substrate is affixed through an UV-hardening resin to the signal face of an optical stamper and is examined using an optical head having optical constants equivalent to those of a disk examination machine, thus making it possible to obtain characteristic playback examination results equivalent to those obtained from disks manufactured using the optical stamper, wherefore optical stamper quality can be easily assessed.

19 Claims, 6 Drawing Sheets

OPTICAL DISK STAMPER EXAMINATION MACHINE, OPTICAL DISK STAMPER EXAMINATION METHOD, AND OPTICAL DISK STAMPER

BACKGROUND OF THE INVENTION

1. Field of the Invention

This invention concerns an optical disk stamper examination machine for examining optical disk stampers, an optical disk stamper examination method, and an optical disk stamper.

2. Description of the Related Art

The process of producing optical disks ordinarily is dividable into two main processes, namely the process of making the stamper that is called mastering, and the process of making the disks by molding and film formation using the stamper so made. When any kind of trouble arises in the mastering process, using that stamper to manufacture disks and then examining the finished products result in losses, which losses are greater the larger the scale of disk production. Thus it is desirable to examine the stamper with a stamper examination machine prior to disk manufacture and to use that stamper in the disk production process only after verifying that it meets specifications. For this reason the examination of stampers plays a very important role. The method of examining stampers using a conventional optical disk stamper examination machine, wherein such playback characteristics as tracking error signals and HF signals from the pits formed in the optical disk stamper are examined, is now described with reference to FIG. 6.

Figure 6:
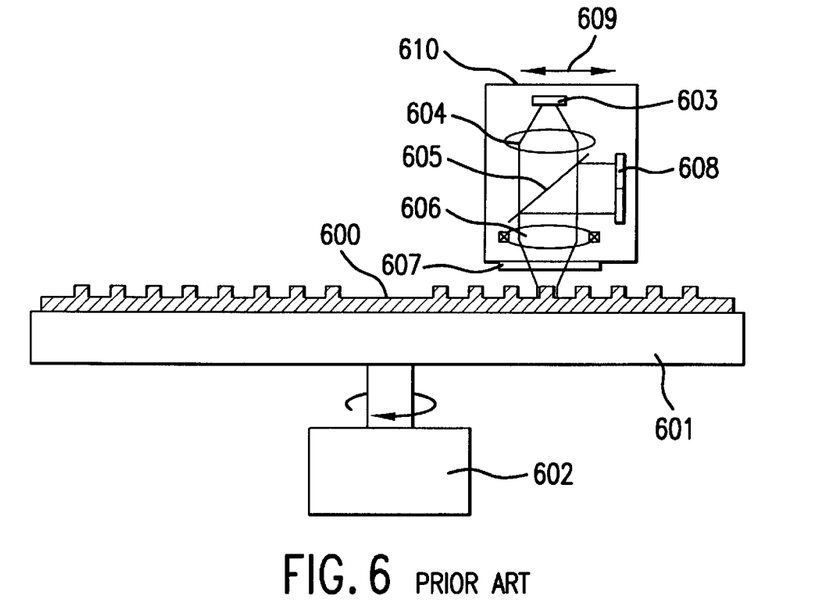
FIG. 6 is a diagram for describing a conventional optical disk stamper examination machine.

The optical disk stamper 600 being examined is attached to a revolving table 601, a laser beam is aimed at the optical disk stamper by an optical head 610 while the optical disk stamper 600 is being rotated by a spindle motor 602, and the amount of light reflected thereby is detected. In the optical head 610, diffused light is emitted by a semiconductor laser 603, and that light is converted to a parallel beam by a collimating lens 604. After this beam passes through a beam splitter 605, it is condensed by an objective lens 606, passes through a plane parallel plate 607, and strikes the signal face of the optical disk stamper 600. The laser spot striking the signal face of the optical disk stamper 600 is reflected as it is modulated by the shapes of the pits and grooves in the signal face, and passes back through the plane parallel plate 607 and objective lens 606 to be reflected by the beam splitter 605 so that the quantity of light can be detected by a photodiode 608. The plane of incidence in the photodiode 608 is divided into two areas, each of which performs current-voltage conversions and amplification, forming two channels. HF signals are obtained by adding the output signals of the respective channels while preserving the high band. Tracking error signals are obtained by subtracting the output signals of these two channels, one from the other.

The objective lens 606 used here is usually an objective lens having the same design specifications as those mounted in optical disk drives. These objective lenses that are used in optical disk drives are designed so that diffraction-limited focal points are formed in the reflection layer, through the optical disk substrate. For this reason, in optical disk examination machines also, a plane parallel plate 607 that is effective in correcting wave aberration, just as the aforesaid substrate, is typically provided between the objective lens 606 and the optical disk stamper 600. With this configuration, diffraction-limited focal points having the same size as when performing disk examinations can be formed on the signal face of the optical disk stamper 600.

In addition to methods wherein a plane parallel plate 607 or the like is fixed to an optical head, as in the example described above, an examination method has been devised wherein, instead of the plane parallel plate 607, a transparent substrate is simply superimposed on the stamper and secured to the revolving table together with the stamper.

When optical disk stampers are examined using the methods described above, the playback characteristics are considerably different than the playback characteristics measured from actual optical disk stampers by the disk examination machine. The underlying principle here is explained with reference to FIGS. 4 and 5, taking the HF signal modulation factor that is one examination category of playback-only optical disks as an example. The playback-only optical disks discussed here are those of a type wherein concave and convex marks of differing lengths are continuously cut into the disk in a spiral form.

Figure 4A:
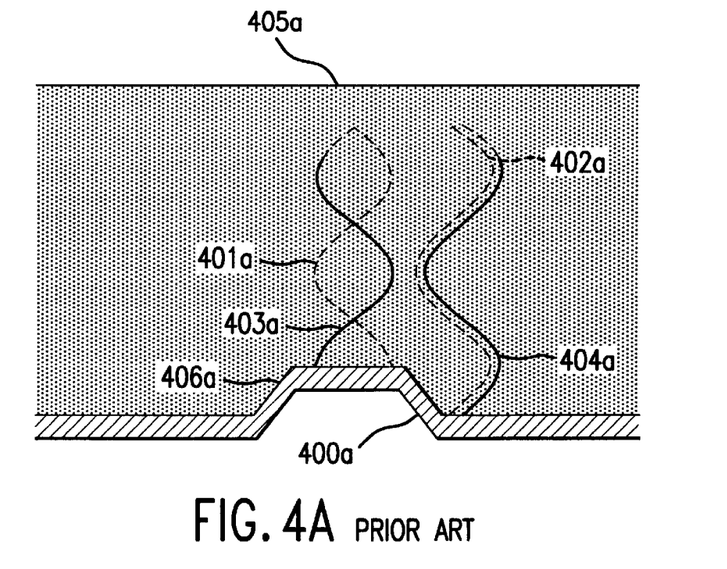
FIGS. 4A and 4B are a pair of diagrams for describing the playback principles of a conventional optical disk stamper examination machine and optical disk examination machine.

The case of examining an optical disk with a disk examination machine is first described. The laser beam emitted from the optical head of the disk examination machine strikes the substrate surface 405a of the optical disk, passes through the interior of the substrate, and arrives at a mark 406a on the head unit. When an examination is being conducted, measurements are made using a focusing servo so that the incident beams form a focal point in a reflection layer 400a. A beam waist is therefore formed in the reflection layer 400a. Looking at this portion microscopically, we can think of it schematically as a parallel beam. Here the beam component 401a prior to arrival at the mark 406a and the beam component 402a prior to arrival in space that is another portion are in phase with each other. After this, when each of the beam components is reflected, differences in light path arise in the round-trip portion of the height of the mark 406a, whereupon phase modulation is imposed. The beam components 401a and 402a are converted by reflection into beam components 403a and 404a, respectively, that are mutually out of phase.

When actually recorded marks are played back, tracking is effected on the continuous marks in a state wherein the focusing servo is applied to the reflection layer 400a. An example of an HF signal waveform is diagrammed in FIG. 5A at 501a. At the moment that the beam passes the mark 406a, due to the phase shift between the two beam components 403a and 404a, an action occurs whereby the components cancel each other out, the quantity of light incident on the photodiode is reduced, and a minimum 503a is formed in the waveform 501a.

Figure 5A:
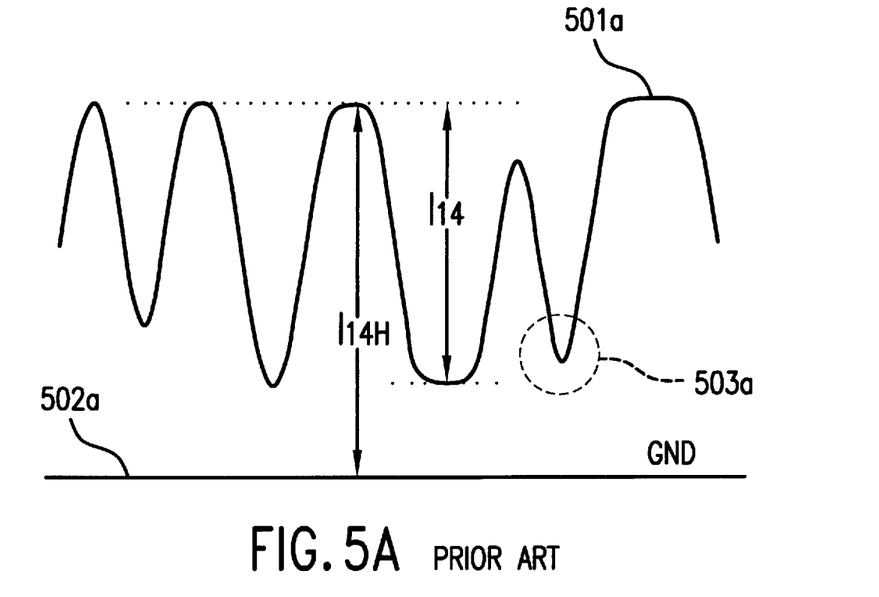
FIGS. 5A–5B are a pair of diagrams representing HF signal playback waveforms for a conventional optical disk stamper examination machine and optical disk examination machine.

It is usually desirable that the height of the mark 406a be designed such that the phase difference between the beam components 403a and 404a becomes as close as possible to π in order to realize a large modulation factor in the HF signal having the waveform 501a. We here take the HF signal modulation factor to be the 14T mark modulation factor (where T is the channel pit period), and define that as $$I_{14}/I_{14H}.$$

This phase difference is dependent on the wavelength of the beam in the interior of the substrate, wherefore it is necessary to take the wavelength in the substrate into consideration when setting the height of the mark 406a. If we designate the beam wavelength in a vacuum as $\lambda_0$ and the refractive index of the substrate as $n_s$, then the wavelength $\lambda_s$ inside the substrate may be expressed as $$\lambda_s = \lambda_0/n_s.$$

Then, when the phase difference is π, for example, the height h of the mark 406a becomes $$h = \lambda_0/4n_s.$$

Figure 4B:
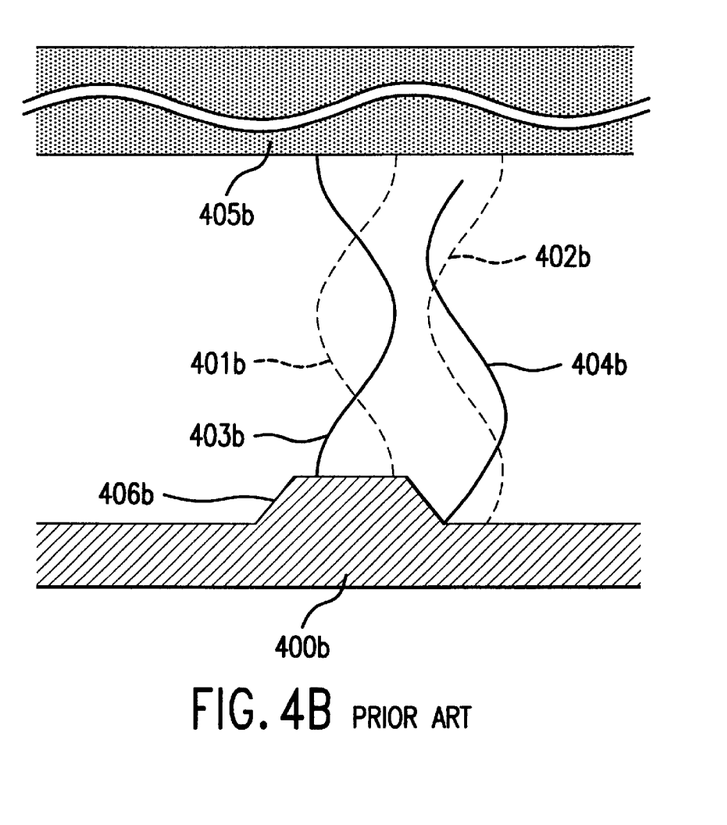

A case is described next wherein a stamper is examined directly with a stamper examination machine. The laser beam emitted from the optical head of the stamper examination machine passes through a plane parallel plate to correct for wave aberration and arrives at a stamper 400b. When an examination is being performed, the focus servo is operated to direct the beam onto the signal face of the stamper 400b. Here the beam component 401b prior to arrival at the mark 404b and the beam component 402b prior to arrival in space that is another portion are in phase with each other. After this, when each of the beam components is reflected, differences in light path arise in the round-trip portion of the height of the mark 406a, whereupon phase modulation is equivalently imposed. The beam components 401b and 402b will then be converted by reflection into beam components 403b and 404b, respectively, that are mutually out of phase.

Figure 5B:
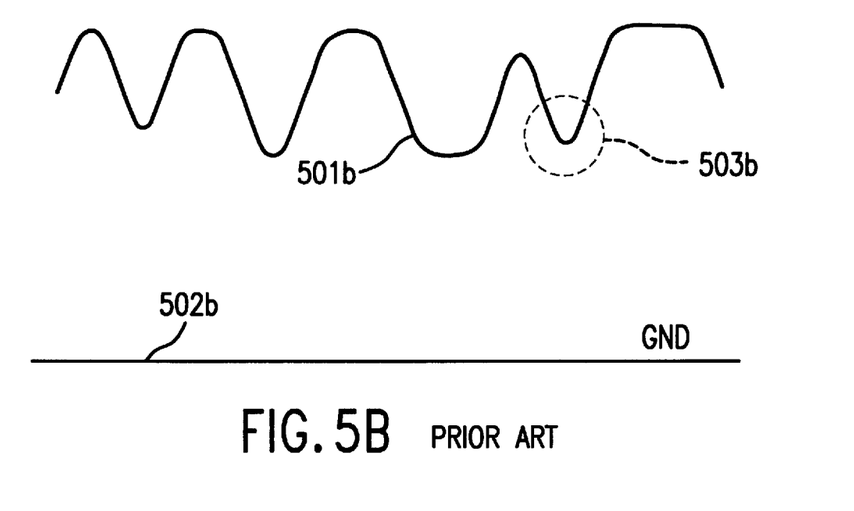

The playback signal waveform at this time is diagrammed in FIG. 5B at 501b. As in the disk examination, due to the phase shift between the two beam components 403b and 404b at the moment that the beam passes the mark 406a, the quantity of light incident on the detector decreases, and a minimum 503b is formed in the waveform 501b. In this case, however, the beam passes through air to reach the stamper, so the wavelength will be almost identical to the wavelength $\lambda_0$ in a vacuum. The refractive index will be about 1.5 since a polycarbonate or glass is commonly used for the substrate. That being so, playback during stamper examination will be with a beam having a wavelength that is 1.5 times longer than during disk examinations, which has a large effect on playback characteristics. If the mark height is $\lambda_0/4n_s$, that is, the same as in the disk described earlier, the phase difference between the reflected beam components 403b and 404b will not be π, whereupon the mutual canceling action will behave imperfectly. As a result, the HF signal modulation factor will not be the same as that obtained in the disk examination, as in the waveform 501b, but will be a smaller value.

Thus, if exact one-to-one correlations between the measured values for the disks and the stampers can be discovered, in terms of the differences in measured values of HF signal modulation factors caused by the disparity in playback principle between the disk and the stamper examination machines, then the disk HF signal modulation factor can be derived from the results of the stamper examination without any problem. This cannot be done, however, because the correlations differ depending on such shape parameters as the angle of the mark slopes and the sharpness of the marks. Thus it is very difficult to derive the exact disk modulation factor with a stamper examination machine. This problem is not limited to HF signal modulation factors either, but applies to all playback signal examination categories.

SUMMARY OF THE INVENTION

An object of the present invention is to easily obtain, in stamper examinations, the same results as when examining disks, thereby facilitating the assessment of stamper quality.

The optical disk stamper examination machine comprises a transparent substrate that is superimposed on the optical disk stamper to be examined, a transparent substance that is sandwiched in between the optical disk stamper and the substrate, and an optical head that, through the substrate and the resin, irradiates the optical disk stamper with a laser beam and detects the reflected light therefrom.

The optical disk stamper examination machine also contains a transparent substance which is a resin.

The optical disk stamper examination machine also contains a resin that is a UV-hardening resin.

The optical disk stamper examination machine also contains a transparent substance that is a liquid.

The optical disk stamper is irradiated with a laser beam and examined on the basis of the light reflected therefrom, comprising the steps of: affixing a transparent substrate through a transparent substance to the optical disk stamper; and examining the optical disk stamper using the optical head of the optical disk stamper examination machine which irradiates the optical disk stamper with a laser beam through the substrate and through the resin and detects the light reflected therefrom.

The optical disk stamper examination method described above further comprises the steps of applying a liquid to an optical disk stamper signal face, and affixing a transparent substrate to the optical disk stamper signal face.

The optical disk stamper examination method described above further comprises the steps of applying a liquid to the transparent substrate, and affixing the optical disk stamper to the transparent substrate.

The optical disk stamper examination method described above further comprises the steps of applying a resin to an optical disk stamper signal face, and affixing the transparent substrate to the optical disk stamper signal face.

The optical disk stamper examination method described above further comprises the steps of applying a resin to the transparent substrate, and affixing the optical disk stamper to the transparent substrate.

The optical disk stamper examination method described above further comprises the steps of applying a UV-hardening resin to the optical disk stamper, affixing the transparent substrate to the optical disk stamper, and hardening the UV-hardening resin by irradiating it from the side of the transparent substrate.

The optical disk stamper examination method described above further comprises the steps of applying a UV-hardening resin to the transparent substrate, affixing the optical disk stamper to the transparent substrate, and hardening the UV-hardening resin by irradiating it from the side of the transparent substrate.

The optical disk stamper examination machine further comprises: a film-like transparent substance that covers the recording surface of the optical disk stamper being examined; and an optical head that passes a laser beam through the transparent substance to irradiate the optical disk stamper and detects the light reflected therefrom.

The optical disk stamper examination machine may contain a transparent substance which is a light-hardening resin.

The optical disk stamper examination machine may further contain a transparent substance is a volatilization-hardening resin that is hardened by the volatilization of a solvent.

The optical disk stamper may be irradiated with a laser beam and examined on the basis of the light reflected therefrom, comprising the steps of: forming a film-like transparent substance that covers the recording surface of the optical disk stamper; and examining the optical disk stamper using the optical head of the optical disk stamper examination machine which irradiates the optical disk stamper with a laser beam through the substrate and through the resin and detects the light reflected therefrom.

The optical disk stamper examination method may further comprise the steps of applying a light-hardening resin to the recording surface of the optical disk stamper, and hardening the light-hardening resin by irradiating it with light.

The optical disk stamper examination method may further comprise the steps of applying a volatilization-hardening resin to the recording surface of the optical disk stamper, and hardening the volatilization-hardening resin by causing a solvent to volatilize.

DESCRIPTION OF THE PREFERRED EMBODIMENTS

A first embodiment is now described. The optical disk stamper examination machine according to claim 3 is described as the first embodiment of the present invention, with reference to FIG. 1.

Figure 1:
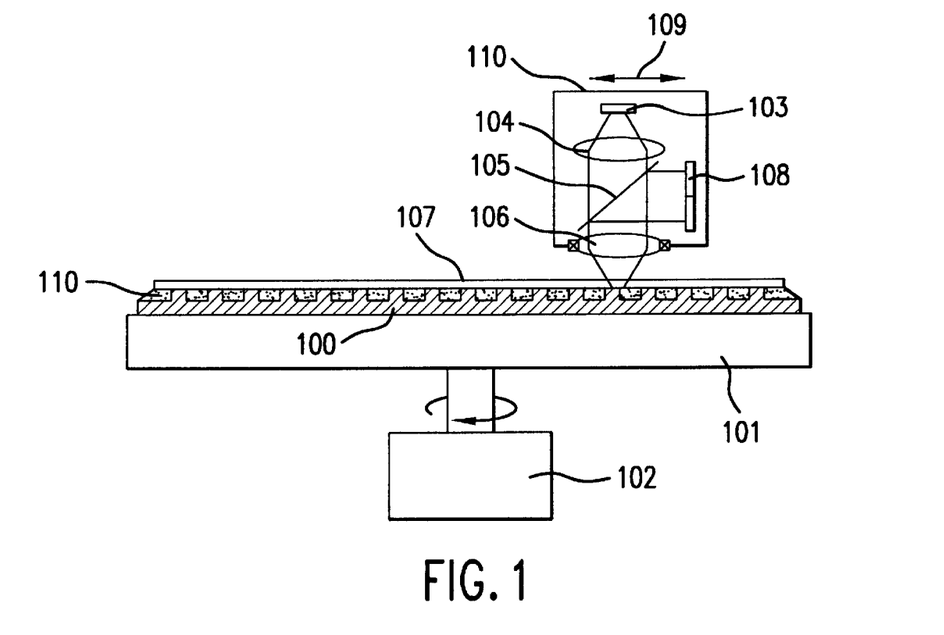
FIG. 1 is a diagram for describing an optical disk stamper examination machine in a first embodiment.

The optical disk stamper examination machine of the present invention mainly comprises an optical head 110 and a spindle motor 102 to the main shaft of which is attached a revolving table 101. A glass substrate 107 is affixed to a disk stamper 100 that is to be subjected to measurement, through a pre-hardened UV-hardening resin 110.

The functions of the optical head 110 are now described. Diffuse light is emitted from a semiconductor laser 103, converted to a parallel beam by a collimating lens 104, passed through a beam splitter 105, and condensed by an objective lens 106. The beam, after passing through the substrate 107 and being reflected by the signal face of the optical disk stamper 100, passes back through the substrate 107 and strikes the objective lens 106. After passing through the objective lens 106, the beam is reflected by the beam splitter 105, whereupon the quantity of light is detected by a photodiode 108. Thereafter HF signals and tracking error signals are detected as in the related art discussed in the foregoing.

The revolving table 101 is fixed at its center to the main shaft of the spindle motor 12. The revolving table 101 is also provided with air suction or magnetic features for securing stampers thereto. The spindle motor 102 generates turning drive forces when measurements are being made.

When a stamper is played back with this examination machine, the refractive index of the glass substrate 107 is approximately 1.5, wherefore, if a UV-hardening resin 110 is used having a refractive index near the same value, playback is possible at a wavelength of $\lambda_0/n_s$ and the optical parameters will match those in effect during disk examination. Nickel is commonly used as the stamper material, wherefore high reflectance is obtainable, and the stamper will function in the same way as the reflecting layer of a disk.

In this embodiment the medium sandwiched in between the stamper 100 and the glass substrate 107 is a UV-hardening resin 110, but is not limited thereto, and there is no restriction on the material used so long as it exhibits a refractive index equivalent to that of the glass substrate 107. The material used in the glass substrate 107 is not restricted either so long as a refractive index equivalent to that of the disk can be elicited.

The stampers subjected to measurement are not limited to playback-only optical disk stampers. The present invention is effective for all optical disk stampers, including write-once, read-many optical disks and rewritable optical disks.

Thus by examining stampers with the stamper examination machine of the present invention, it is possible to easily obtain examination results that are like disk examination results without actually manufacturing any disks.

A second embodiment is now described. The optical disk stamper examination machine according to claim 3 is described as the second embodiment of the present invention, with reference to FIG. 2.

Figure 2:
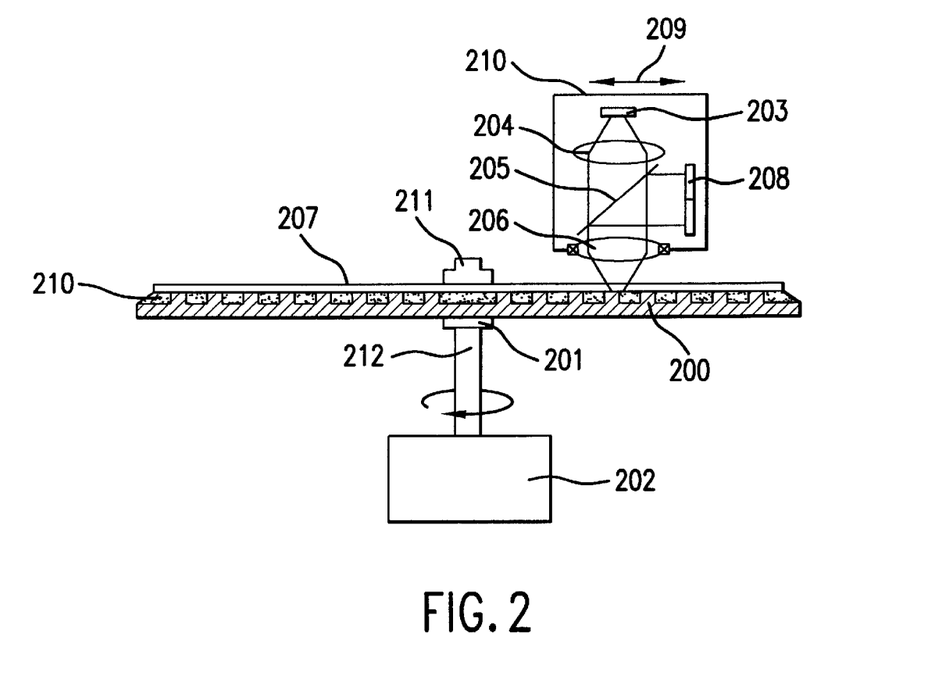
FIG. 2 is a diagram for describing an optical disk stamper examination machine in a second embodiment.

The optical disk stamper examination machine of the present invention mainly comprises an optical head 210 and a revolving unit made up of a spindle motor 202, main shaft 212, and receptacle unit 201.

A glass substrate 207 is affixed to a disk stamper 200 that is to be subjected to measurement, through a pre-hardened UV-hardening resin 210.

The functions of the optical head 210 are now described. Diffuse light is emitted from a semiconductor laser 203, converted to a parallel beam by a collimating lens 204, passed through a beam splitter 205, and condensed by an objective lens 206. The beam, after passing through the glass substrate 207 and being reflected by the signal face of the optical disk stamper 200, passes back through the glass substrate 207 and strikes the objective lens 206. After passing through the objective lens 206, the beam is reflected by the beam splitter 205, whereupon the quantity of light is detected by a photodiode 208. Thereafter HF signals and tracking error signals are detected as in the related art discussed in the foregoing.

The receptacle unit 201 is fixed to the main shaft 212, comes in contact with the stamper near the center thereof, and holds the optical disk stamper 200 so that its signal face is kept perpendicular to the main shaft of the spindle motor. The optical disk stamper 200 and glass substrate 207 have center holes through which the main shaft 212 is passed and fixed by a removable clamp 211. The spindle motor 202 generates turning drive forces when measurements are being made.

When a stamper is played back with this examination machine, the refractive index of the glass substrate 207 is approximately 1.5, wherefore, if a UV-hardening resin 210 is used having a refractive index near the same value, playback is possible at a wavelength of $\lambda_0/n_s$ and the optical parameters will match those in effect during disk examination. Nickel is commonly used as the stamper material, wherefore high reflectance is obtainable, and the stamper will function the same way as the reflecting layer of a disk.

In this embodiment the medium sandwiched in between the stamper 200 and the glass substrate 207 is a UV-hardening resin 210, but is not limited thereto, and there is no restriction on the material used so long as it exhibits a refractive index equivalent to that of the glass substrate 207. The material used in the glass substrate 207 is not restricted either so long as a refractive index equivalent to that of the disk can be elicited.

The stampers subjected to measurement are not limited to playback-only optical disk stampers. The present invention is effective for all optical disk stampers, including write-once, read-many optical disks and rewritable optical disks.

Because the stamper itself does not have adequate strength to maintain its signal face flat, in conventional stamper examination machines it has been necessary to provide flat turntables having the same size, in terms of diameter, as the stampers. The stampers are affixed to the turntables by air suction or magnets, etc., thereby flattening the stamper signal faces. With the optical disk stamper examination machine of the present invention, however, the optical disk stamper 200 is affixed to the glass substrate 207 by a UV-hardening resin 210, wherefore the flatness of the signal face of the optical disk stamper 200 is preserved by the flatness of the glass substrate 207. That being so, there is no need for a large revolving table or for complex mechanisms such as air suction or magnets to attach the stamper, thus providing the advantage of being able to simplify the examination machine structure.

A third embodiment is now described. Each process step in the optical disk stamper examination method cited in claim 10, set forth here as the third embodiment of the present invention, is described, making reference to FIG. 3. FIG. 3 is a set if diagrams of cross-sections passing through the center of the stamper at each process step.

Figure 3A:
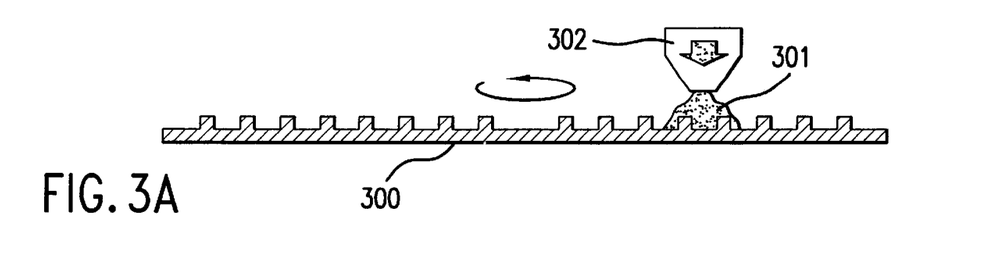
FIGS. 3A–3E are a set of diagrams representing process steps, for describing an optical disk stamper examination method in a third embodiment.
Figure 3B:
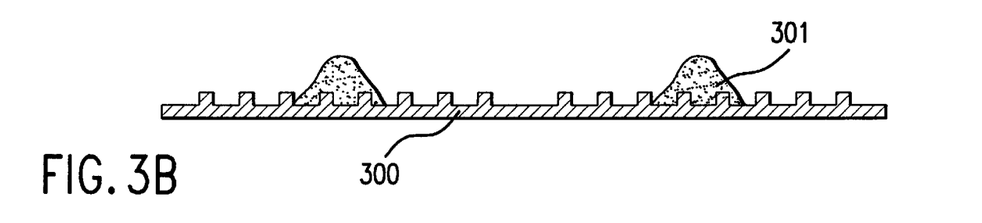

First, an optical disk stamper 300 that is to be subjected to measurement is placed on the horizontal revolving table with its signal face up. If it appears that the optical disk stamper is warped, it is made flat with the use of a clamp or clamps at the outer or inner circumference.

As diagrammed in FIG. 3A, while turning the revolving table, a nozzle 302 is placed near the center circumference, from which UV-hardening resin 301 is discharged. The UV-hardening resin 301 is thus built up in a ring on the signal face of the optical disk stamper, as diagrammed in FIG. 3B. The optical disk stamper 300 is then placed in a vacuum chamber and subjected to reduced pressure.

Figure 3C:
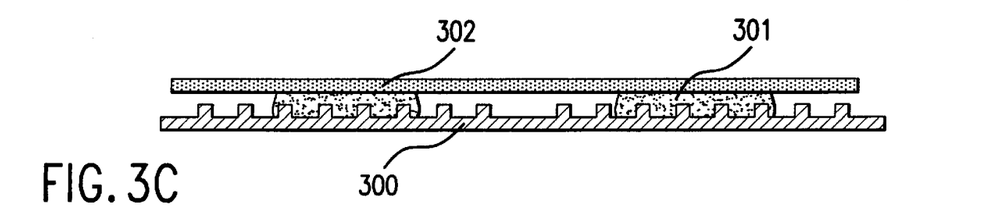
Figure 3D:
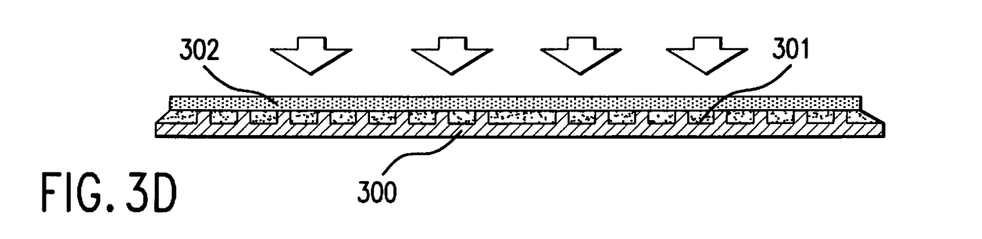

As diagrammed in FIG. 3C, a glass substrate 302 is dropped down from directly overhead while being maintained horizontal. Once the UV-hardening resin 301 has adapted itself to the whole optical disk stamper 300, it is removed from the vacuum chamber and exposed to UV radiation through the glass substrate 302, as diagrammed in FIG. 3D.

Figure 3E:
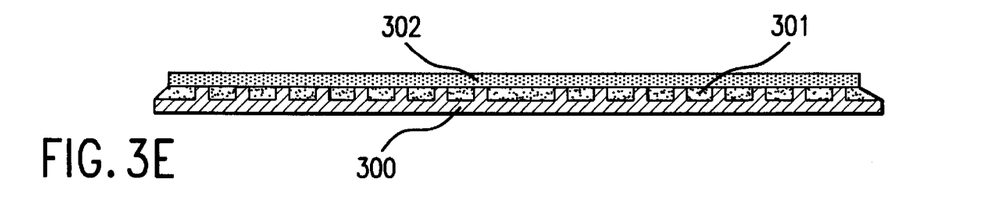

When these process steps have been completed, the optical disk stamper 300 is finished, with the glass substrate 302 affixed to it through the UV-hardening resin 301 in a tightly sealed condition.

Subsequently, the optical disk stamper 300 is examined by an optical disk evaluating machine, just as optical disks are, whereupon it is possible to obtain examination results from the optical disk stamper 300 equivalent to those obtained from optical disks.

With the examination method of this embodiment, UV-hardening resin is built up on the stamper, after which a glass substrate is affixed. The examination method of the present invention is not thereby limited, however, it being possible instead to build up the UV-hardening resin on the glass substrate and affix the stamper after that.

Thus, by affixing the glass substrate 302 to the optical disk stamper 300, the signal face can be protected from the scratches and contamination that tend to occur while handling the optical disk stampers. If stored in this condition, moreover, it is possible to suppress corrosion and deterioration in the signal face for long periods of time.

A fourth embodiment is now described. The optical disk stamper examination machine cited in claim 16 is described as the fourth embodiment of the present invention, making reference to FIG. 7.

Figure 7:
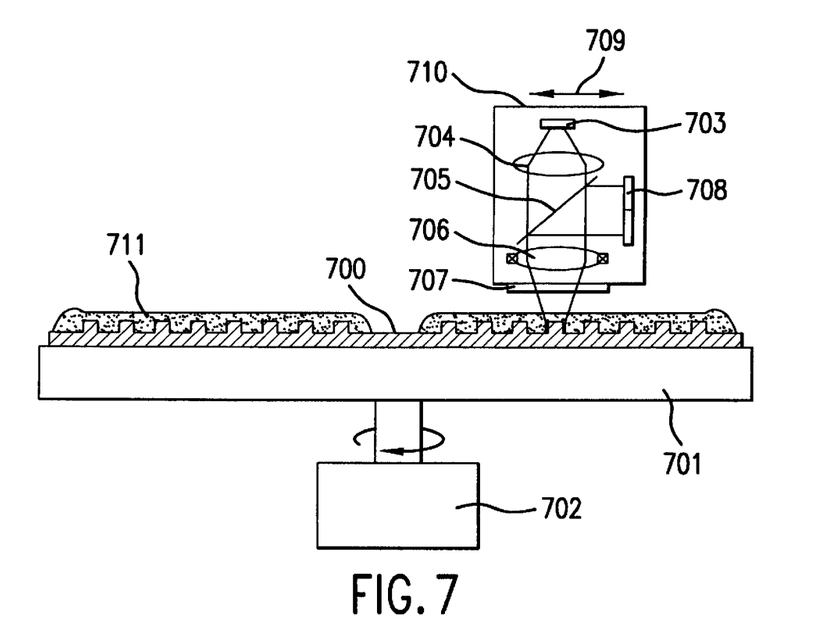
FIG. 7 is a diagram for describing an optical disk stamper examination machine in a fourth embodiment.

The optical disk stamper examination machine of the present invention mainly comprises an optical head 710, and a revolving unit made up of a spindle motor 702 and a revolving table 701. The optical disk stamper 700 is preliminarily spin-coated with a volatilization-hardening resin 711 that is hardened by the volatilization of a solvent, and then subjected to volatilization.

The functions of the optical head 710 are now described. Diffuse light is emitted from a semiconductor laser 703, converted to a parallel beam by a collimating lens 704, passed through a beam splitter 705, and condensed by an objective lens 706. The beam passes through a wave-aberration correcting plate 707 and passes on through the volatilization-hardening resin 711 formed on the recording surface on which pits or grooves are recorded in the optical disk stamper 700, and then forms a focal point on the recording surface of the optical disk stamper 700. At this time, the optical disk stamper 700 is revolving, with pits or grooves having been formed on its surface, wherefore the beams striking it are reflected while undergoing optical modulation. Then, after the beam passes through the volatilization-hardening resin 711, it passes through the wave-aberration correcting plate 707 and reaches the objective lens 706.

After passing through the objective lens 706, the beam is reflected by the beam splitter 705, and the quantity of light is detected by a photodiode 708. Thereafter HF signals and tracking error signals are detected as in the related art discussed in the foregoing.

The objective lens 706 is usually one designed to be used with so-called optical disks, wherein light passes through the optical disk substrate and forms a diffraction-limited focal point. Therefore, when such an objective lens is used, a wave-aberration correcting plate 707 that plays the same role as the optical disk substrate becomes necessary.

The revolving table 701 is fixed to the main shaft of the spindle motor 702, comes into contact with the stamper near the center thereof, and holds the optical disk stamper 700 so that its recording surface is kept perpendicular to the main shaft of the spindle motor. The spindle motor 702 generates turning drive forces when measurements are being made.

When a stamper is played back with this examination machine, if a volatilization-hardening resin 711 is used which exhibits a refractive index $n_s$ of approximately 1.5 after hardening, playback is possible at a wavelength of $\lambda_0/n_s$ and the optical parameters will match those in effect during disk examination. Nickel is commonly used as the stamper material, wherefore high reflectance is obtainable, and the stamper will function the same way as the reflecting layer of a disk.

By testing the groove playback signal characteristics of the optical disk stamper using the volatilization-hardening resin, not only will the examination results be the same as those obtained from a disk fabricated with this same stamper, but the adhering film of volatilization-hardening resin is effective in protecting the stamper from becoming defective.

The volatilization-hardening resin 711 can also be peeled away after it is hardened, thus providing a cleaning action in removing defects from the optical disk stamper surface.

In this embodiment, a volatilization-hardening resin 711 was used as the transparent substance coated onto the optical disk stamper 700, but the transparent substance is not limited thereto, and may be any substance so long as it is one exhibiting an equivalent refractive index.

The stampers subjected to measurement are not limited to playback-only optical disk stampers. The present invention is effective for all optical disk stampers, including write-once, read-many optical disks and rewritable optical disks.

A fifth embodiment is now described. Each process step in the optical disk stamper examination method cited in claim 19, set forth here as the fifth embodiment of the present invention, is described, making reference to FIG. 8. FIG. 8 is a set of diagrams of cross-sections passing through the center of the stamper at each process step. Subsequently, the signal face of the optical disk stamper is spin-coated with a volatilization-hardening resin.

Example procedures for spin coating are now described. As diagrammed in FIG. 8A, while turning the revolving table at slow R.P.M., volatilization-hardening resin 801 is discharged from a nozzle 802 as it moves from the outer circumference to the inner circumference. As diagrammed in FIG. 8B, the volatilization-hardening resin 801 is built up over the entire signal face of the optical disk stamper 800. Then, while turning the revolving table at high R.P.M., excess volatilization-hardening resin 801 is flung off, and a film of uniform thickness is formed as diagrammed in FIG. 8C.

Figure 8A:
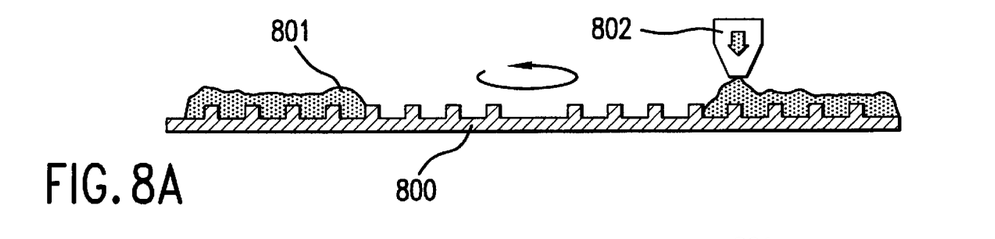
FIGS. 8A–8E are a set of diagrams representing process steps, for describing an optical disk stamper examination method in a fifth embodiment.
Figure 8B:
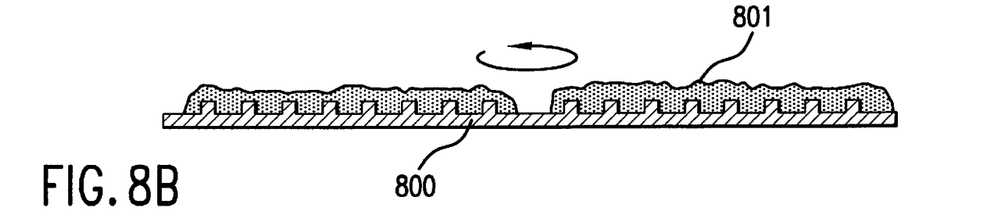
Figure 8C:
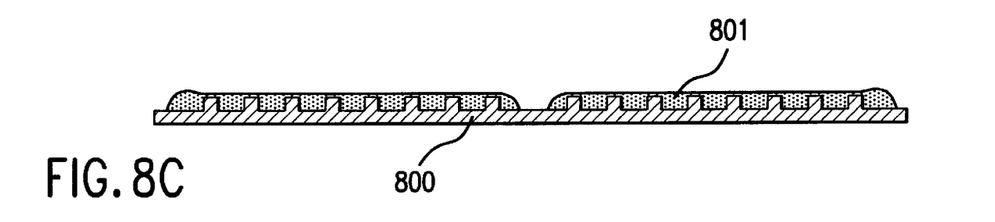
Figure 8D:
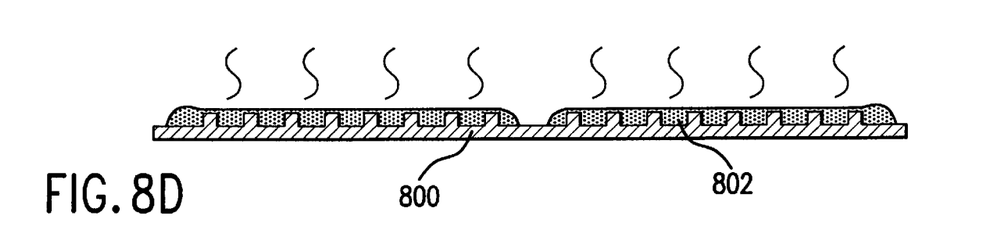

Next, as diagrammed in FIG. 8D, by allowing the volatilization-hardening resin 801 to stand, its solvent is volatilized, causing it to harden. Alternatively, in the interest of shortening the process time, the drying may be done in a drying oven. When the solvent has been volatilized, a volatilization-hardening resin 803 layer is formed.

Figure 8E:
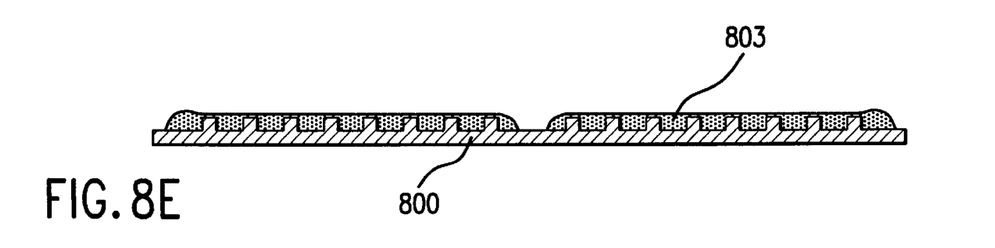

The stamper is next placed on the revolving table 701 of an optical disk evaluation machine such as diagrammed in FIG. 7, with the signal face up. If the optical disk stamper appears to be warped, it is flattened using a mechanism such as vacuum suction or magnets to affix the optical disk stamper 800 to the revolving table 701. After that, by examining the groove playback signal characteristics in the same way as a disk is examined, the same examination results can be obtained as from optical disks made with this optical disk stamper 800.

From the perspective of wave aberration at the focal point formed on the recording surface of the optical disk stamper 800, every possible effort should be made to make the thickness of the volatilization-hardening resin 803 layer as thin as possible relative to that of the wave-aberration correcting plate 707. However, if light beams reflected from the recording surface of the optical disk stamper 800 interfere with those reflected from the upper surface of the volatilization-hardening resin 803, this will affect the playback signal, wherefore it is desirable that the volatilization-hardening resin 803 layer be thicker in order to reduce these interfering components. Taking both of these conflicting influences into consideration, the resin thickness should be made on the order of several tens of microns.

By covering the signal face of the optical disk stamper in this manner, scratches and contamination can be prevented from impairing the signal face when the optical disk stampers are handled. Moreover, when they are stored in this condition, signal face corrosion and deterioration can be suppressed for long periods of time.

In the examination method of this embodiment, a volatilization-hardening resin was spin-coated onto the optical disk stamper, but the examination method of the present invention is not limited thereby, and it is possible that an UV-hardening resin be used instead.

The entire disclosure of Japanese Patent Application No. 295488/1977 filed on Oct. 28, 1997 and No. 224903/1998, including specification, claims, drawings and summary, are incorporated herein by reference in its entirety.

As represented in the optical disk stamper examination machines and examination methods of the present invention, optical disk stampers can be examined with an optical disk examining machine, just as an optical disk is examined, by first affixing a glass substrate thereto with a UV-hardening resin. Moreover, from the same playback principle as for a disk, the same playback characteristic examination results can be obtained as from optical disks made from the selfsame optical disk stamper. This being so, by examining the stampers after the optical disk mastering operation is finished, in the process of manufacturing the optical disks, inferences can be made concerning the optical disks that will be made therewith, and the quality of the stampers can be assessed.

Also, because the stamper signal face is covered by a glass substrate, the scratches and soiling that occur from mishandling can be prevented. Corrosion and deterioration in the stamper signal face can also be prevented during long-term storage.

What is claimed is:

1. An optical disk stamper examination machine that examines an optical disk stamper, comprising:

a transparent material composed of a single layer superimposed over the optical disk stamper, the single layer composed of a film-like transparent substance that covers the recording surface of the optical disk stamper being examined; and an optical head that irradiates the optical disk stamper with a light of a laser beam through the transparent material, and detects a reflected light.

2. The optical disk stamper examination machine according to claim 1, wherein the transparent material is composed of two layers, the first layer is a transparent substrate superimposed on the optical disk stamper to be examined; and the second layer is a transparent substance sandwiched between the optical disk stamper and the substrate.

3. The optical disk stamper examination machine according to claim 2, wherein said transparent substance is a resin.

4. The optical disk stamper examination machine according to claim 3, wherein said resin is a UV-hardening resin.

5. The optical disk stamper examination machine according to claim 2, wherein said transparent substance is a liquid.

6. The optical disk stamper examination machine according to claim 1, wherein said transparent substance is a light-hardening resin.

7. The optical disk stamper examination machine according to claim 1, wherein said transparent substance is a volatilization-hardening resin that is hardened by volatilizing a solvent.

8. An optical disk stamper examination machine that examines an optical disk stamper, comprising:

an optical disk stamper;

a transparent single layer composed of a film-like transparent substance superimposed over a recording surface of the optical disk stamper; and an optical head that irradiates the optical disk stamper with a light of a laser beam through the transparent substance, and detects reflected light.

9. An optical disk stamper examination method for examining an optical disk stamper, comprising:

affixing a transparent material having a single layer composed of a film-like transparent substance over the recording surface of an optical disk stamper;

irradiating the optical disk stamper with a light of a laser beam through the transparent material; and detecting a reflected light.

10. An optical disk stamper examination method for examining an optical disk stamper, comprising:

affixing a transparent material composed of a single layer over the optical disk stamper, the single layer composed of a film-like transparent substance that covers the recording surface of the optical disk stamper;

irradiating the optical disk stamper with a light of a laser beam through the transparent material; and detecting a reflected light.

11. The optical disk stamper examination method according to claim 10, wherein the transparent material is composed of a transparent substrate and a transparent substance, and the transparent substrate is affixed to the optical disk stamper through the transparent substance.

12. The optical disk stamper examination method according to claim 11, further comprising:

applying a liquid to an optical disk stamper signal face, and affixing a transparent substrate to said optical disk stamper signal face.

13. The optical disk stamper examination method according to claim 11, further comprising:

applying a liquid to said transparent substrate, and affixing said optical disk stamper to said transparent substrate.

14. The optical disk stamper examination method according to claim 11, further comprising:

applying a resin to an optical disk stamper signal face, and affixing said transparent substrate to said optical disk stamper signal face.

15. The optical disk stamper examination method according to claim 11, further comprising:

applying a resin to said transparent substrate, and affixing said optical disk stamper to said transparent substrate.

16. The optical disk stamper examination method according to claim 11, further comprising:

applying a UV-hardening resin to said optical disk stamper, affixing said transparent substrate to said optical disk stamper, and hardening said UV-hardening resin by irradiating same from the side of said transparent substrate.

17. The optical disk stamper examination method according to claim 11, further comprising:

applying a UV-hardening resin to said transparent substrate, affixing said optical disk stamper to said transparent substrate, and hardening said UV-hardening resin by irradiating same from the side of said transparent substrate.

18. The optical disk stamper examination method according to claim 10, wherein said first step comprises the steps of applying a light-hardening resin to said recording surface of said optical disk stamper, and hardening said light hardening resin by irradiating it with light.

19. The optical disk stamper examination method according to claim 10, wherein said first step comprises the steps of applying a volatilization-hardening resin to said recording surface of said optical disk stamper, and hardening said volatilization-hardening resin by causing a solvent to volatilize.

* * * * *